(12) United States Patent
Prestipino et al.

(10) Patent No.: US 6,428,315 B1
(45) Date of Patent: *Aug. 6, 2002

(54) DENTAL IMPRESSION TRAY

(76) Inventors: David Michael Prestipino, 521 Bushy Ridge Dr., Star Tannery, VA (US) 22654; Vincent Joseph Prestipino, 14635 Crossway Rd., Rockville, MD (US) 20853

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/606,192

(22) Filed: Jun. 29, 2000

(51) Int. Cl.⁷ .................................................. A61C 9/00
(52) U.S. Cl. ........................................... 433/45; 433/37
(58) Field of Search .............................. 433/45, 41, 42, 433/43, 46, 37, 38, 71, 214, 47

(56) References Cited

U.S. PATENT DOCUMENTS

| | | | | |
|---|---|---|---|---|
| 53,347 A | * | 3/1866 | Schaffer | 433/45 |
| 98,066 A | | 12/1869 | Jenks | |
| 1,489,192 A | * | 4/1924 | Cleveland | 433/45 |
| 1,499,482 A | | 7/1924 | Simmons | |
| 1,652,910 A | | 12/1927 | Psayla | |
| 3,626,594 A | | 12/1971 | Zinner et al. | |
| 3,878,610 A | * | 4/1975 | Coscina | 433/37 |
| 3,978,585 A | | 9/1976 | Holcomb | |
| 4,368,040 A | | 1/1983 | Weissman | |
| 4,432,728 A | * | 2/1984 | Skarky | 433/37 |
| 4,689,010 A | * | 8/1987 | Wolfe | 433/38 |
| 5,336,086 A | | 8/1994 | Simmen et al. | 433/37 |
| 5,340,308 A | | 8/1994 | Cukjati | 433/41 |
| 5,551,872 A | * | 9/1996 | Mena | 433/37 |
| 5,890,895 A | | 4/1999 | Tucker | 433/37 |

FOREIGN PATENT DOCUMENTS

| | | |
|---|---|---|
| AT | 149778 | 5/1937 |
| WO | WO 92/3985 | 3/1992 |

* cited by examiner

Primary Examiner—John J. Wilson
Assistant Examiner—Melba Bumgarner
(74) Attorney, Agent, or Firm—Stephen Christopher Swift; Swift Law Office (57) ABSTRACT

An improved dental impression tray, to be placed under an upper jaw or over a lower jaw, combining the following features: 1. Creases or lines of perforations running through the base and side walls of the tray and the middle of the tray's handle, so that the tray can easily be broken in portions, if an impression of only one side of a jaw needs to be taken. 2. Ridges or protrusions on opposite interior walls of the tray, to better retain the rapidly hardening semi-fluid material with which the impressions of the teeth and/or gums are taken. 3. Base panels of the tray separated from the walls of the tray by gaps around their perimeters, and connected only by narrow strips of the material from which the tray is made, so that the base panels can be easily detached when desired, thus creating an opening in the bottom of the tray that may be desirable for certain forms of oral surgery, especially work involving dental implants. 4. A crease or line of perforations adjacent to the ridges or protrusions, so that flanges, forming parts of the walls opposite the base and extending beyond the ridges or protrusions, may be readily detached. Alternative embodiments may have less than all of the foregoing features.

16 Claims, 6 Drawing Sheets

DENTAL IMPRESSION TRAY

BACKGROUND OF THE INVENTION

1. Field of the Invention

The present invention relates to trays for holding material used to make impressions of teeth and gums.

2. Description of the Prior Art

When a dentist makes an impression of a patient's teeth and/or gums, he or she places a temporarily viscous compound called an "impression material" over the teeth and gums in each jaw. To obtain an accurate impression, the impression material must be pushed against the teeth and gums, so that there are no gaps between the teeth and gums and the impression material. After the impression material has hardened enough to retain its shape, it is then removed and used as a mold. It is customary to place the compound in a tray before it is placed over the teeth and gums. Dental impression trays are shaped to fit over the teeth and gums in a jaw.

It is desirable to have an improved method of retaining the impression material in the tray before it hardens. It is sometimes necessary to make an impression of teeth on only one side of a jaw. It is also sometimes desirable to have an opening in the tray, especially when work is being done on dental implants. It is sometimes necessary in surgical situations to make an impression of the occlusal (biting or grinding) half of the teeth and certain implant components while avoiding contact with the underlying tissue. It will be seen that the present invention meets these needs better than the prior art.

U.S. Pat. No. 53,347, issued on Mar. 20, 1866, to George F. Schaffer, discloses a dental impression cup with detachable bottom sections.

U.S. Pat. No. 98,066, issued on Dec. 21, 1869, to Robert V. Jenks, discloses one of the first dental impression trays to be patented, made in two separate pieces, which is divided in the middle as is the present invention. The two separate pieces can be joined by lugs and a clamping screw, or by other means. The instant invention is distinguishable, in that it has a different means of attaching the two halves, which cannot be rejoined when separated.

U.S. Pat. No. 1,489,192, issued on Apr. 1, 1924, to Ernest A. Cleveland, discloses an adjustable dental tray with removable side walls.

U.S. Pat. No. 1,499,482, issued on Jul. 1, 1924, to Henry Charles Simmons, discloses another dental impression tray having two halves, which are joined by a clamping screw.

U.S. Pat. No. 1,652,910, issued on Dec. 13, 1927, to Joseph E. Psayla, discloses a registering bite tray, having rectangular perforations similar in shape to the gap made when one of the detachable panels in removed from the present invention. The instant invention is distinguishable, in that it has detachable panels, so that the position of the openings can be varied to suit patient's circumstances.

U.S. Pat. No. 3,626,594, issued on Dec. 14, 1971, to Ira D. Zinner and Herbert Sherman, discloses a dental impression tray having separable end portions.

U.S. Pat. No. 3,878,610, issued on Apr. 22, 1975, to William Alfred Coscina, discloses a low profile dental impression tray, with vertical score lines through which sections of the tray can be broken off.

U.S. Pat. No. 3,978,585, issued on Sep. 7, 1976, to Burton V. Holcomb, discloses a dental impression tray with numerous perforations and a handle extending from the front.

U.S. Pat. No. 4,368,040, issued on Jan. 11, 1983, to Bernard Weissman, discloses a dental impression tray, which in one embodiment has two halves that can be locked together.

U.S. Pat. No. 4,432,728, issued on Feb. 21, 1984, to Floyd E. Sharky, discloses a dental tray with vertical grooves along which sections of the tray can be broken off.

U.S. Pat. No. 4,689,010, issued on Aug. 25, 1987, to Herbert Wolfe, discloses a dental impression tray with "ribs" on the inside surfaces of the sidewalls.

U.S. Pat. No. 5,336,086, issued on Aug. 9, 1994, to Christian Simmen and Nathaniel H. Lenchner, discloses a dental impression tray, having numerous perforations, and ribs elevated above the inside bottom surface between the walls of the tray.

U.S. Pat. No. 5,340,308, issued on Aug. 23, 1994, to Joseph F. Cukjati, discloses an adjustable dental tray with sliding portions that enable its shape to be adjusted to fit the shape of the mouth of the patient. (This tray is designed for mammals in general, not primarily for humans.)

U.S. Pat. No. 5,551,872, issued on Sep. 3, 1996, to Raul Mena, discloses a dental impression device having a housing member with openings in an upper wall, and a cover member.

U.S. Pat. No. 5,890,895, issued on Apr. 6, 1999, to John Hilliard Tucker, discloses a dental impression tray, with a handle and a mouth piece having various perforations through which excess impression material is extruded and interlocks to secure the impression material to the mouthpiece.

International patent application Ser. No. WO 92/3985, published on Mar. 19, 1992, discloses a dental modeling method and apparatus using an apertured matrix plate.

Austrian Patent No. 149,778, issued on May 25, 1937, to Alfred Pelzmann and Karl Kaindlstorfer, discloses a dental impression tray with a handle and holes or slits through which excess impression material can flow.

None of the above inventions and patents, taken either singly or in combination, is seen to describe the instant invention as claimed.

SUMMARY OF THE INVENTION

The invention is an improved dental impression tray, with several unique features: 1. A crease or line of perforations running through the middle of the tray (where it is placed over the front part of an upper or lower jaw) and the middle of the tray's handle, so that the tray can easily be broken in half, if an impression of only one side of a jaw needs to be taken. (There may also be additional creases or lines of perforations situated in vertical planes perpendicular to the circumference of the tray, so that fractions of the tray smaller than one half can be detached to take an impression of less than one half of a jaw.) 2. Ridges or protrusions on opposite interior walls of the tray, to better retain the rapidly hardening semi-fluid material with which the impressions of the teeth and/or gums are taken. 3. Base panels of the tray separated from the walls of the tray by gaps around their perimeters, and connected only by narrow strips of the material from which the tray is made, so that the base panels can be easily detached when desired, thus creating an opening in the occlusal aspect (or bottom) of the tray that may be desirable for certain forms of dentistry, especially work involving dental implants. 4. A crease or line of perforations running just above the ridges or protrusions, to facilitate easy and clean removal of a flange extending above the ridges or protrusions.

Accordingly, it is a first object of the invention to provide a means of taking an impression of only one side of a jaw.

It is a second object of the invention to reduce the size of the dental impression tray to the minimum size necessary.

It is third object of the invention to provide a means of retaining impression material more securely in the impression tray.

It is a fourth object of the invention to provide an improved means of making one or more openings in an impression tray.

It is a fifth object of the invention is to provide an impression tray which is useful in work on dental implants.

It is a sixth object of the invention to provide a method of quick and easy removal of the buccal and lingual (inner and outer) flanges without creating small grindings of the parent material or the cutting material so as to keep the surgical site clean.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention is an improved dental impression tray. Dental impression trays are used to hold the impression material used by dentists to make impressions of teeth and/or gums. Impression material (which may be a polymer or hydro-colloidal mixture) is in a semi-fluid state when first prepared, but hardens within several minutes. Impression trays are necessary to hold the material before it hardens. The impression tray is preferably made of plastic, but it may be made of any suitable material. The impression material is first inserted into the tray. Then the tray is placed over the patient's teeth and gums of either the upper or lower jaw, and pushed to insure that there are no gaps between the impression material and the teeth and gums. It is then left in place until the impression material hardens. The tray with the impression material is then removed, and the impression material is used as a mold.

Figure 1:
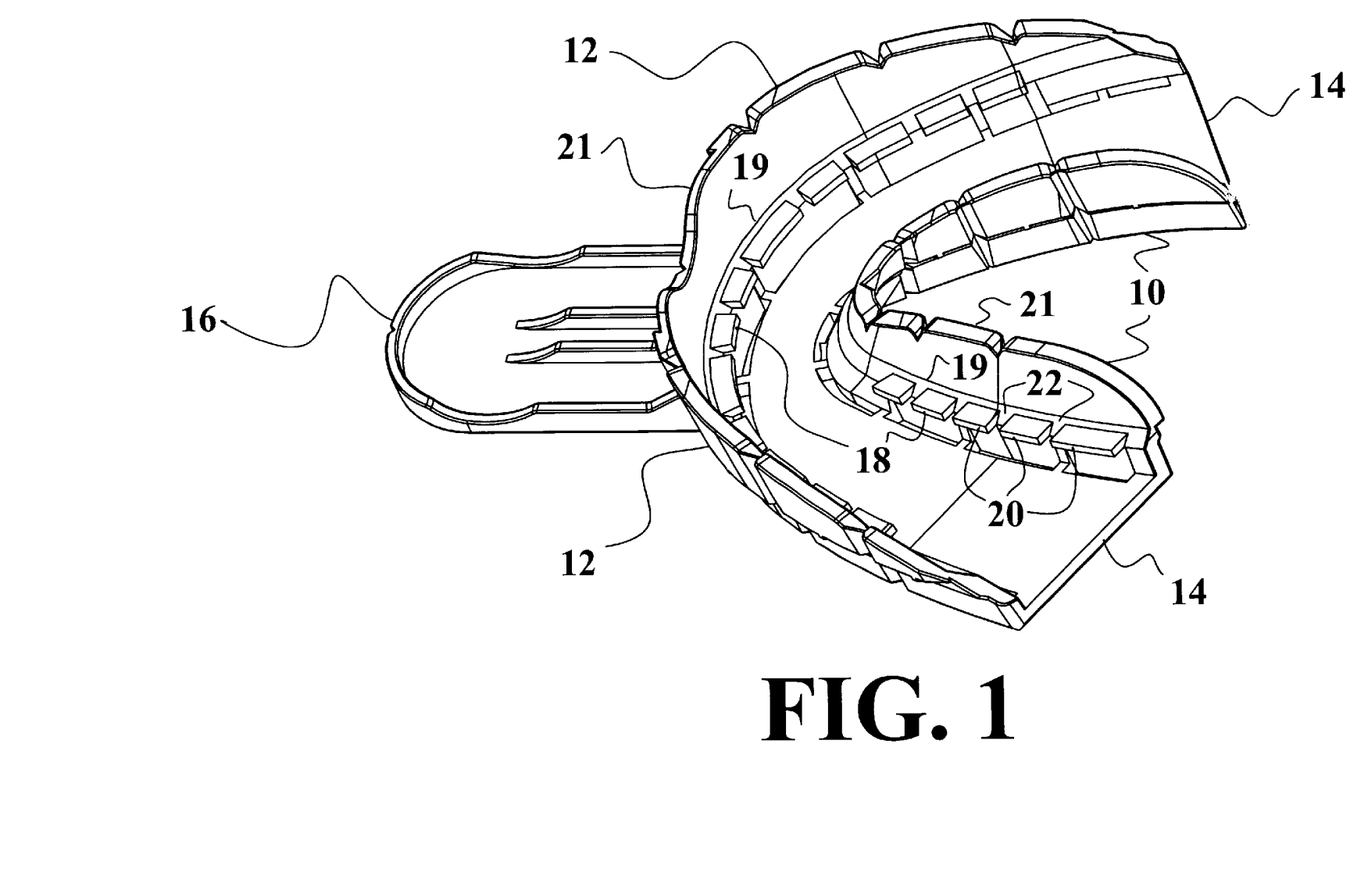
FIG. 1 is a perspective view of the preferred embodiment of the invention.

FIG. 1 is a perspective view of the preferred embodiment of the invention, showing an inner wall 10, an outer wall 12, and a base 14. A handle 16 is attached to the outer wall. Ridges 18 comprised of protrusions 20 separated by gaps 22 extend inward from the interior surfaces of the inner and outer walls. The purpose of the ridges is to more securely retain the impression material in the tray before it hardens. In the preferred embodiment, the protrusions are all parallel to the base and are all equidistant from the base. Creases (or lines of perforations) 19 adjacent to the ridges allow quick and easy removal of flanges 21 that are parts of the inner and outer walls extending beyond the ridges. If an impression is to be made during surgery (as is common in implant dentistry) it is sometimes necessary to keep both the tray and the impression material away from the surgically involved tissue. By removing the flanges, the dentist can effectively limit the volume and position of the impression material, so as to keep the surgical site sterile.

Figure 2:
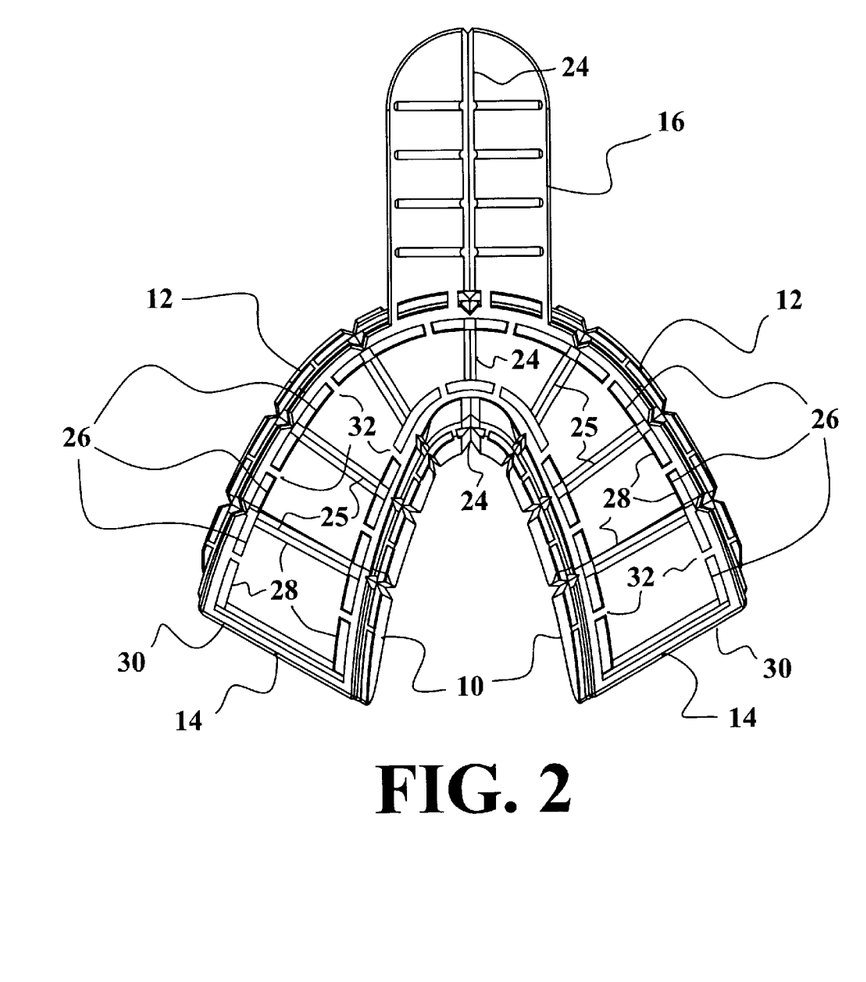
FIG. 2 is a bottom p plan view of the preferred embodiment of the invention.

FIG. 2 is a bottom plan view of the preferred embodiment of the invention, showing the central crease 24, an area of reduced thickness running (within a vertical plane) through the center of the walls, the base, and the handle. The tray may be manually broken along the central crease, if an impression of only one side of a jaw is needed. There are also side creases 25, which are areas of reduced thickness running (within a vertical plane perpendicular to the circumference of the tray) through the walls and the base. The tray may be manually broken along the side creases, if an impression of less than one half of a jaw is needed. Alternatively, perforations (within the same vertical planes) through the wall, base and handle may serve the same function of creating an area of reduced strength along which the tray may be neatly divided. In dentistry, it is often only necessary to take an impression of one side of a jaw.

Also shown in FIG. 2 are eight panels 26 into which the base is divided. (Alternatively, the number of panels may be greater or lesser than eight.) The panels are separated from each other and from the inner and outer walls by gaps 28. The inner and outer walls are joined by end segments 30. The panels are joined to the walls only by connecting strips 32. The connecting strips are sufficiently weak that one or more panels may be easily removed when it is desired to create an opening in the base of the tray. It is desirable to be able to create such an opening in taking an impression for work on dental implants, as an impression coping will extend from the implant to beyond the level of the base of the tray. (A dental implant is imbedded in the bone of a jaw, and an artificial tooth is attached to the implant to replace a natural tooth that has been lost. An impression of the gums and adjacent teeth is needed to form a mold against which the artificial tooth can be fitted when it is being formed in a dental laboratory. An impression coping is used to register the three-dimensional location of the implant relative to the adjacent teeth and gums.) With prior art impression trays, it is necessary to drill a hole through the tray when working with dental implants, creating small particles of material that can be accidently swallowed by the patient. The detachable panels of the present invention provide a more convenient and cleaner way of creating an opening in the tray. (Note that the crease and the panels, though part of the preferred embodiment, are not shown in the other drawings.)

Figure 3:
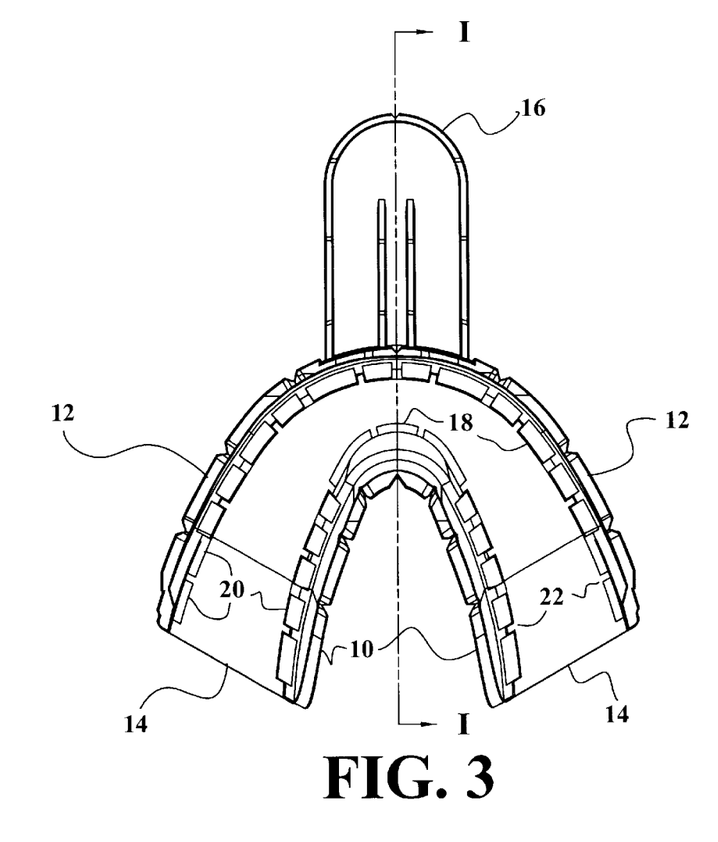
FIG. 3 is a top plan view of the preferred embodiment of the invention.
Figure 4:
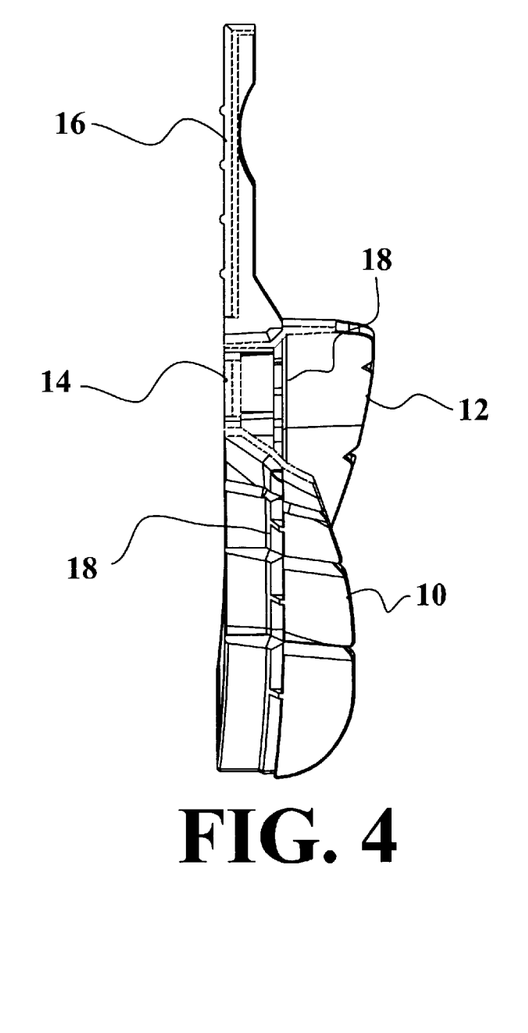
FIG. 4 is a section view of the preferred embodiment of the invention along the line I—I in FIG. 3.
Figure 5:
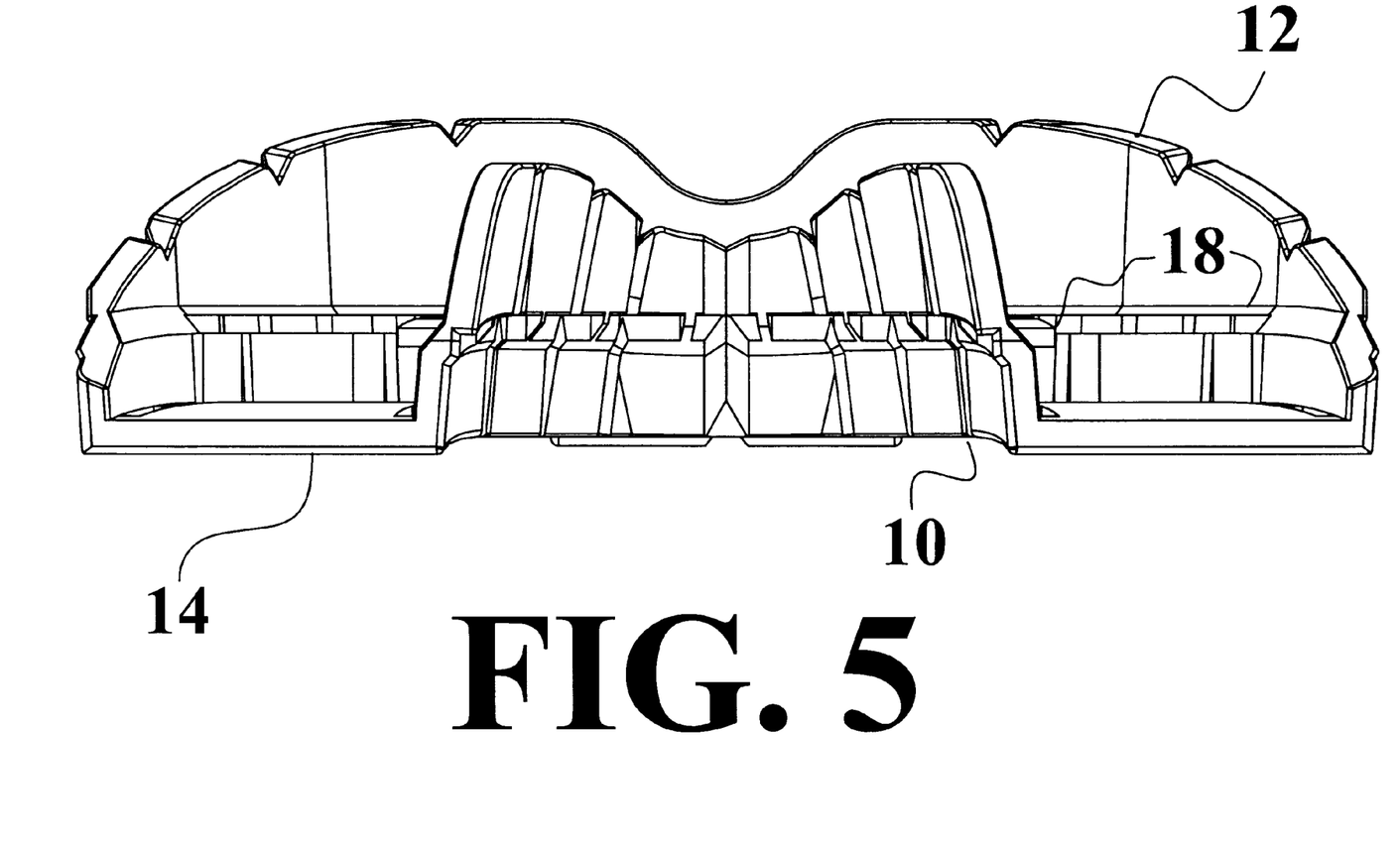
FIG. 5 is a front elevational view of the preferred embodiment of the invention.
Figure 6:
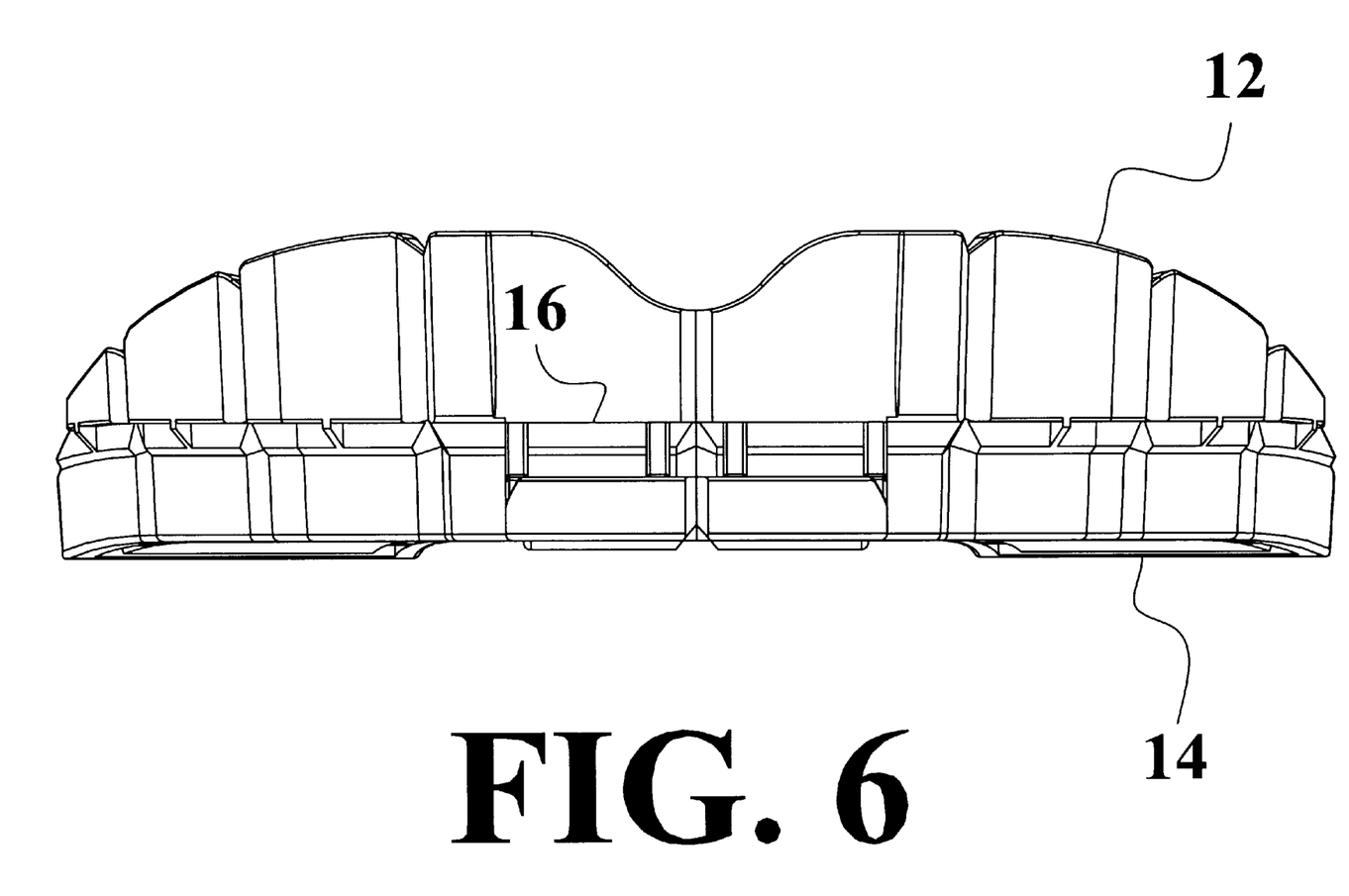
FIG. 6 is a rear elevational view of the preferred embodiment of the invention.

FIG. 3 is a top plan view of the preferred embodiment of the invention. FIG. 4 is a section view of the preferred embodiment of the invention along the line I—I in FIG. 3. FIG. 5 is a front elevational view of the preferred embodiment of the invention. FIG. 6 is a rear elevational view of the preferred embodiment of the invention. The features shown in FIGS. 3–8 are described supra.

While the preferred embodiment contains all of the features described above, especially creases or lines of perforations running through the middle and sides of the tray and the middle of the tray's handle, ridges and/or protrusions on opposite interior walls of the tray, panels in the base of the tray connected only by narrow strips to the frame of the base, and removable flanges, alternative embodiments having only one or two of the these features are within the scope of the invention. It is to be understood that the present invention is not limited to the sole embodiment described above, but encompasses any and all embodiments within the scope of the following claims.

We claim:

1. A dental impression tray, comprising an inner wall and an outer wall connected by a base, the walls and the base being suitably dimensioned and configured to be placed around an entire jaw, while retaining material from which an impression of teeth and gums in the jaw can be made; and the base comprises panels and areas of reduced strength between the panels and the walls;

wherein the panels can be detached from the base to from an opening in the base.

2. A dental impression tray according to claim 1, wherein there are protrusions from interior surfaces of the walls, suitably dimensioned and configured to help retain the material from which an impression can be made.

3. A dental impression tray according to claim 2, wherein there is at least one area of reduced strength in an upper part of the walls, lying between the protrusions and upper edges of the walls, the upper edges being opposite lower edges at which the walls are joined to the base, and portions of the upper walls lying above said at least one area of reduced strength can be detached.

4. A dental impression tray according to claim 3, wherein the protrusions extend from both the inner wall and the outer wall.

5. A dental impression tray according to claim 4, wherein the protrusions are equally spaced and parallel to the base.

6. A dental impression tray according to claim 5, wherein said at least one area of reduced strength in the upper part of the walls lies in a plane parallel to the base.

7. A dental impression tray according to claim 6, further comprising at least one area of reduced strength in the walls and the base along a plane perpendicular to the base, at which the dental impression tray can be broken into more than one piece.

8. A dental impression tray according to claim 1, wherein there is at least one area of reduced strength in the walls and the base along a plane perpendicular to the base, at which the dental impression tray can be broken into more than one piece.

9. A dental impression tray, comprising an inner wall and an outer wall connected by a base, the walls and the base being suitably dimensioned and configured to be placed around a portion of a jaw, while retaining material from which an impression of teeth and gums in the jaw can be made; and the base comprises panels and areas of reduced strength between the panels and the walls;

wherein the panels can be detached from the base to form an opening in the base.

10. A dental impression tray according to claim 9, wherein there are protrusions from interior surfaces of the walls, suitably dimensioned and configured to help retain the material from which an impression can be made.

11. A dental impression tray according to claim 10, wherein there is at least one area of reduced strength in an upper part of the walls, lying between the protrusions and upper edges of the walls, the upper edges being opposite lower edges at which the walls are joined to the base, and portions of the upper walls lying above said at least one area of reduced strength can be detached.

12. A dental impression tray according to claim 11, wherein the protrusions extend from both the inner wall and the outer wall.

13. A dental impression tray according to claim 12, wherein the protrusions are equally spaced and parallel to the base.

14. A dental impression tray according to claim 13, wherein said at least one area of reduced strength in the upper part of the walls lies in a plane parallel to the base.

15. A dental impression tray according to claim 14, further comprising at least one area of reduced strength in the walls and the base along a plane perpendicular to the base, at which the dental impression tray can be broken into more than one piece.

16. A dental impression tray according to claim 9, wherein there is at least one area of reduced strength in the walls and the base along a plane perpendicular to the base, at which the dental impression tray can be broken into more than one piece.

* * * * *

UNITED STATES PATENT AND TRADEMARK OFFICE
CERTIFICATE OF CORRECTION

PATENT NO.       : 6,428,315 B1
APPLICATION NO.  : 09/606192
DATED            : August 6, 2002
INVENTOR(S)      : David Michael Prestipino and Vincent Joseph Prestipino

Page 1 of 1

It is certified that error appears in the above-identified patent and that said Letters Patent is hereby corrected as shown below:

Claim 1, column 5, line 17, the second occurrence of "from" should read --form--.

Signed and Sealed this

Nineteenth Day of January, 2010

David J. Kappos
*Director of the United States Patent and Trademark Office*